US005865781A

United States Patent [19]

Lieber et al.

[11] Patent Number: 5,865,781

[45] Date of Patent: Feb. 2, 1999

[54] ELECTRO-MECHANICAL TRACTION DEVICE WITH CONTROLS

[76] Inventors: Mark E. Lieber, 3964 Murry Highlands Cir., Murrysville, Pa. 15668; John H. Petruch, 107 Leneake St., Turtle Creek, Pa. 15145

[21] Appl. No.: 608,512

[22] Filed: Feb. 28, 1996

[51] Int. Cl.[6] ........ A61F 5/00

[52] U.S. Cl. ........ 602/32; 601/33; 601/97; 602/36; 602/33; 602/34; 602/35; 602/38; 602/39; 602/40; 606/241; 606/242

[58] Field of Search ........ 601/33, 97; 602/32–36, 602/38–40; 606/241, 242

[56] References Cited

U.S. PATENT DOCUMENTS

| | | | |
|---|---|---|---|
| 2,204,266 | 6/1940 | Wilcox | 602/39 |
| 3,087,489 | 4/1963 | Gilbert et al. | 602/33 |
| 3,734,088 | 5/1973 | Tucker, Jr. et al. | 606/243 |
| 3,786,803 | 1/1974 | Petulla et al. . | |
| 4,401,110 | 8/1983 | Ekholm | 606/242 |
| 4,583,532 | 4/1986 | Jones | 602/32 |
| 4,608,971 | 9/1986 | Borschneck | 602/38 |
| 5,063,918 | 11/1991 | Guhl | 602/40 |
| 5,181,904 | 1/1993 | Cook et al. . | |
| 5,474,520 | 12/1995 | Bittikofer | 601/33 X |

OTHER PUBLICATIONS

Engineering Data Sheet for Accumax 35, 45, 55 Linear Roller Bearing System by Thomson.

Gordon Products, Incroporated Bulletin No. SW–10 for Analog Proximity Sensors, Jun., 1995.

PLC Direct by Koyo product brochure.

Para Tech Industries, Inc. product brochure for CTD––MARK1 Pneumatic Traction Device.

*Primary Examiner*—Richard J. Apley
*Assistant Examiner*—Denise Pothier
*Attorney, Agent, or Firm*—Buchanan Ingersoll, P.C.

[57] ABSTRACT

An electro-mechanical traction device is provided which includes a motor driven linear actuator connected to a guided carriage. A second carriage is mounted in tandem with the first on a common guide. The two carriages are connected by a spring. A patient engaging device is connected to the second carriage. The linear actuator and carriage guide are mounted to a common surface. When power is provided to the linear actuator motor, it moves the first carriage. The motion is transmitted through the spring to the second carriage and patient engaging device to provide traction to the patient. Reversing the motor relieves the traction force.

7 Claims, 6 Drawing Sheets

ELECTRO-MECHANICAL TRACTION DEVICE WITH CONTROLS

BACKGROUND OF THE INVENTION

1. Field of the Invention

The present invention relates to a traction device for applying traction to a patient. More particularly, the present invention relates to a traction device that provides a gradual application of the traction force to a patient. Still more particularly, the present invention relates to an electro-mechanical traction device that is light-weight, portable and has feedback and control systems for monitoring and actuating the traction treatment.

2. Description of the Prior Art

As a treatment, physical therapists have found it beneficial to apply traction to patients suffering from muscle and nerve injury. During such treatment, it may often be beneficial to the patient to provide traction on a periodic and repetitive basis. Furthermore, a therapist may wish to apply a greater amount of traction to the patient during any one cycle to achieve better results faster than would be the case if only static force were used. Even better therapeutic results can be obtained by providing a relatively "soft" traction force on the patient (i.e., a traction force that does not reach its maximum value instantaneously but which gradually increases to the maximum value).

Devices for applying traction force to a patient are known in the industry. For example, static weight systems for applying traction forces to patients are known, such as is shown and described in U.S. Pat. No. 4,508,109 to Saunders. However, the traction force applied by the device of Saunders is constant. Furthermore, the device is neither relatively light-weight nor portable.

Devices for applying traction forces periodically to a patient are also known in the industry. Such a device, for example, is shown and described in U.S. Pat. No. 3,786,803 to Petulla et al. The apparatus of the Petulla et al. patent utilizes a direct drive traction device having a motor driven spool for spooling a cable connected to a harness attached to a patient. A controller is provided to activate the motor on a periodic basis to provide the traction force.

Also known in the industry are pneumatic traction devices, such a device is shown in U.S. Pat. No. 5,181,904 to Cook et al. The traction device of Cook et al. purports to provide a relatively "soft" traction force to patients. The apparatus of Cook et al. utilizes a carriage traction device attached to the shaft of a pneumatic cylinder powered by a motor driven compressor. The compressor required for the use of pneumatics adds weight and bulk to the device, reducing the portability of the device.

Thus, it would be advantageous to provide a traction device which is relatively light-weight and, therefore, portable. Such a device should further provide a softer traction force to the human body with more tolerance in the traction process than has otherwise been available in the industry.

SUMMARY OF THE INVENTION

The present invention is directed to a traction device which is preferably electro-mechanically operated so as to provide a more light-weight and portable traction device than has heretofore been known in the industry. The present electro-mechanical traction device utilizes a dual carriage system which allows for a "softer" application of the traction force to the patient than has been available in prior traction devices known in the industry.

The portable traction device utilizes a linear actuator which has a movable shaft. The linear actuator may be selectively activated so as to move the shaft in one direction to apply a traction force and to move the shaft in an opposite direction to relax the traction force. The linear actuator is preferably motor-driven.

A carriage assembly is connected to the shaft and is also movably connected to a track. The carriage assembly and the linear actuator are connected to a common surface which is preferably a plate. The carriage assembly has a first movable slide portion that is connected to the linear actuator shaft. The carriage assembly also has a second movable slide portion spaced a selected distance from the first slide portion. A spring is then disposed between the first and the second slide portions. The first and second slide portions are connected so as to be prevented from being moved apart a distance greater than the selected spacing distance but may be moved toward one another by overcoming the spring means. A patient engaging means is then connected to the second movable slide portion. In this way, the traction force may be transmitted to the patient.

Electrical control means are preferably operatively connected to the linear actuator through the motor. In this way, when the motor is actuated, the linear actuator applies a traction force to the traction device and when the motor is reversed, the traction force applied to the traction device is relaxed. The electrical control means is preferably a programmable logic control device which causes the linear actuator to exert a predetermined amount of traction force for a predetermined amount of time and to relax the traction force for a predetermined amount of time. The control circuit is programmable with conventional means so that the amount of force, traction time, release time, and number of repetitions of applications of traction force can be selected by the user.

The control means preferably further includes switch means for manually moving the carriage. When a predetermined distance is reached, the desired force has been applied, and the actuator will stop. Switch means are provided to determine end of travel of the linear actuator.

The portable traction device further preferably utilizes a sensor for determining the amount of traction force applied by the device. The sensor may operate in any convenient fashion, but preferably operates by determining a relative distance between the first slide portion and the second slide portion. Further, it is contemplated that the traction force be measured by transducer means as an alternative or additional means of measuring traction force.

In operation of the device, when power is provided to the linear actuator motor, the linear actuation is moved, moving the first slide portion. As the first slide portion is moved, the motion is transmitted through the spring to the second carriage moving the second carriage. The patient engaging device connected to the second carriage is in turn moved, providing traction to the patient. Reversing the motor relieves the traction force.

The traction device also preferably includes a timer for regulating the amount of time in which the linear actuator maintains traction and likewise releases traction. A counter and an audible signal are also provided to automatically end the treatment (i.e., the cycle of applying and relaxing the traction force) and to signal the end of the treatment.

Other objects and advantages of the invention will become apparent from a description, by way of example only, of certain present preferred embodiments thereof with reference to the accompanying drawings herein.

DESCRIPTION OF THE PREFERRED EMBODIMENTS

Figure 1:
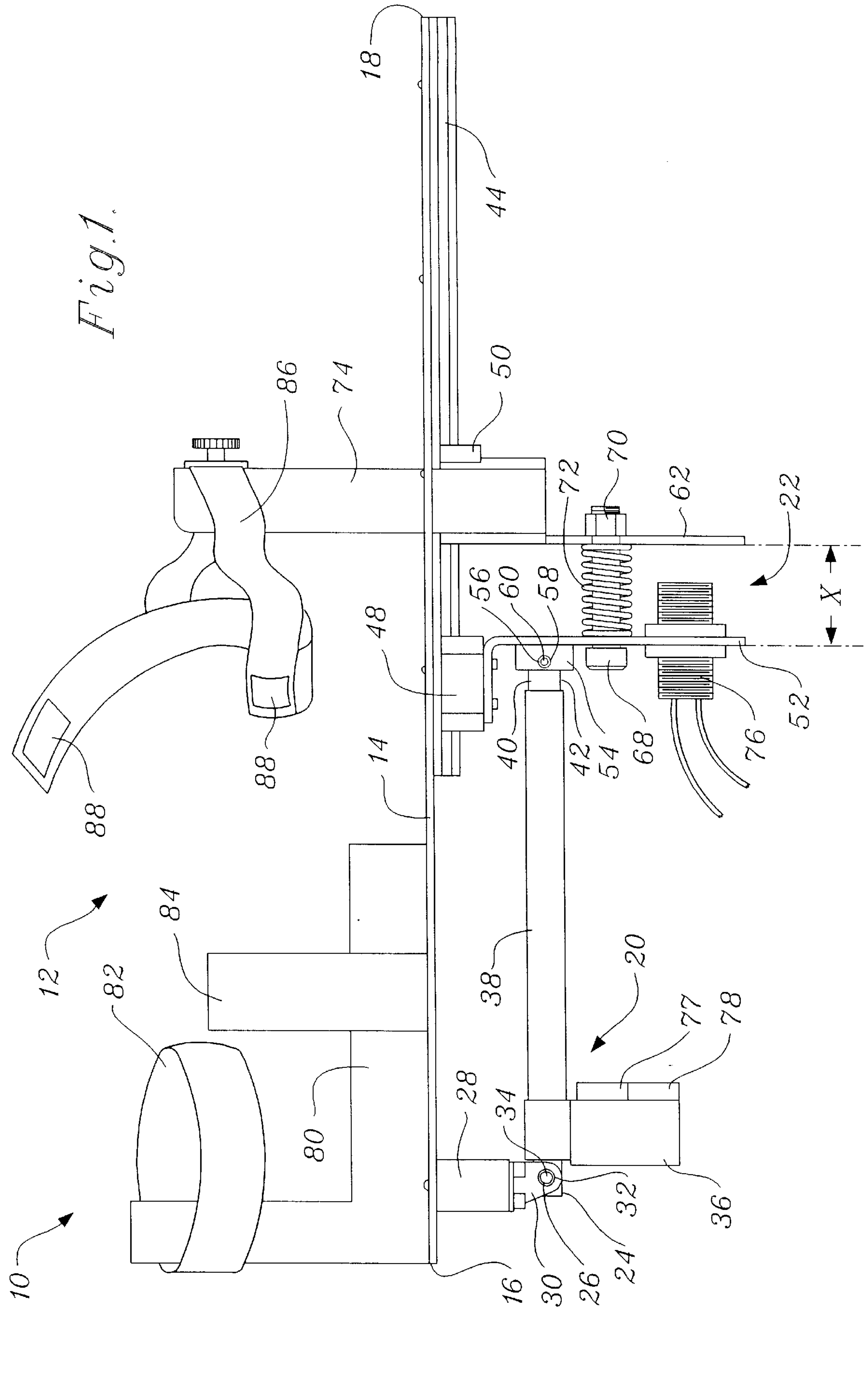
FIG. 1 is a side elevation view of the present preferred electro-mechanical traction device in the retracted position.
Figure 2:
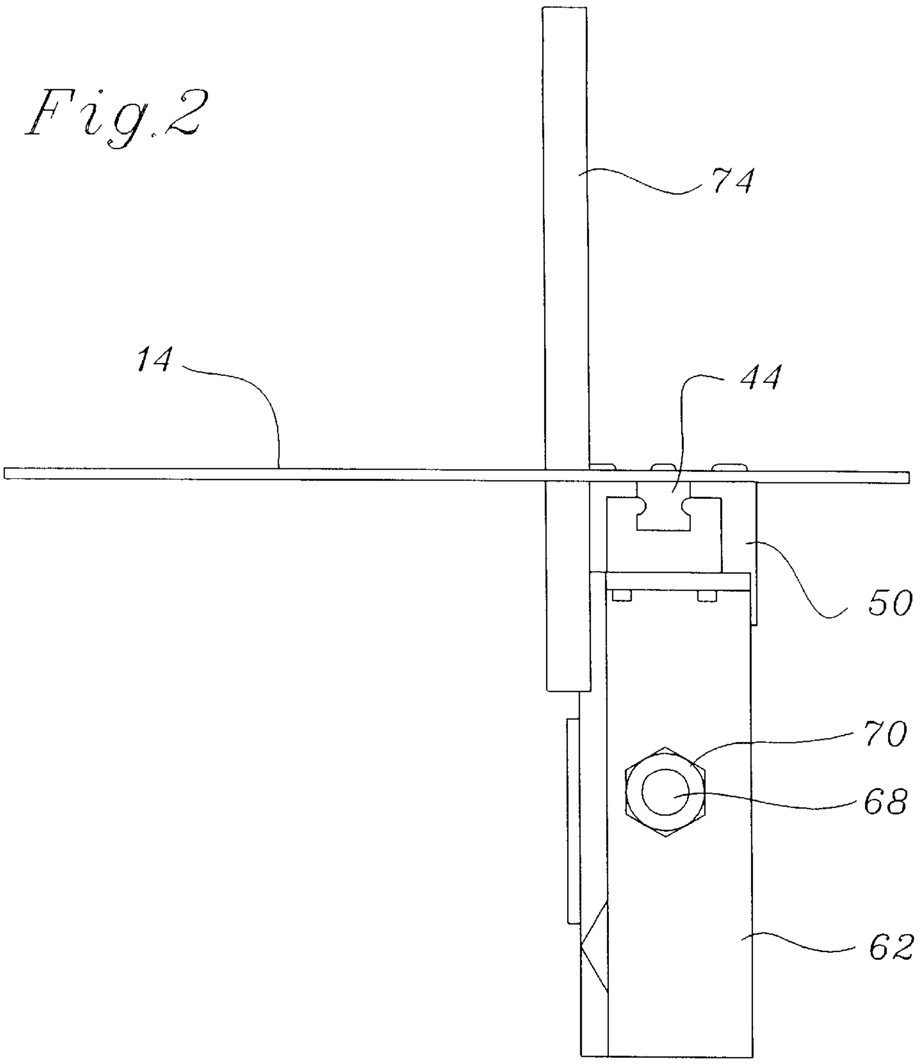
FIG. 2 is a front elevation view of the present preferred electro-mechanical traction device.
Figure 3:
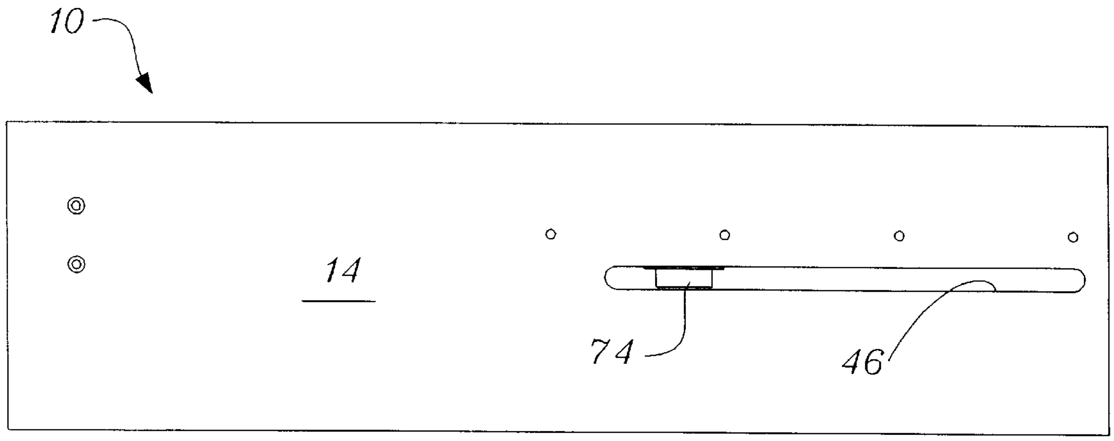
FIG. 3 is a top plan view of the present preferred electro-mechanical traction device.

An electro-mechanical traction device 10 according to the present invention is shown in FIGS. 1, 2 and 3. The device 10 is shown in FIG. 1 having a patient holding device 12. It is distinctly understood that the patient holding device 12 shown in FIG. 1 (for an arm) is just one of many possible patient holding devices which could be used in connection with the present invention. It is intended that by substituting different patient holding devices 12, the traction device 10 could be used to provide traction for various parts of the body. Thus, the patient holding device 12 may be of any suitable configuration or construction suitable to hold and apply traction on selected body parts.

The patient holding device 12 provided as an example in FIG. 1 includes an arm rest 80 which is secured to the frame plate 14. Preferably, arm rest 80 is padded and has side portions (not shown) so that an arm placed upon the arm rest 80 would be prevented from moving laterally relative to the arm rest 80. An upper arm restraint 82 is provided as is a forearm restraint 84 for securing an arm within the patient holding device 12. Attached to member 74 is a wrist restraint 86. Wrist restraint 86 forms a cuff around the wrist of the arm that has traction applied to it by the device 10. The upper arm restraint, the forearm restraint 84 and the wrist restraint 86 are each preferably made of a nylon webbing, although any suitable material may be used. Any means of securing the upper arm restraint 82, the forearm restraint 84 and the wrist restraint 86, respectively, to an arm of a patient can be utilized, however, it is preferred that loop and hook fastening material sections 88 be provided on each restraint 82, 84, 86 in order to secure that restraint around the arm.

The traction device 10 has as its main structural component a base plate 14. The base plate 14 provides the framework for supporting the components of the traction device 10. The base plate 14 is elongated so as to have a first end 16 and a second end 18.

The main components of the traction device 10 are a linear actuator 20 and a carriage assembly 22. The linear actuator 20 is connected to the base plate 14 as will be described in greater detail below. The linear actuator 20 is also connected to the carriage assembly 22 which in turn is movably connected to the base plate 14 as will also be described in greater detail below.

The linear actuator 20 may be mounted to the base plate 14 by any convenient means. Preferably, the linear actuator 20 has a clevis 24 which extends outwards from the linear actuator 20. Clevis 24 preferably has holes 26 provided therethrough. It is further preferred that a spacing bracket 28 is affixed to the base plate 14. The spacing bracket 28 is secured to the base plate 14 by any suitable means such as by being bolted or screwed thereto. The spacing bracket 28 has a mounting portion 30. The mounting portion 30 of the spacing bracket 28 has holes 32 provided therethrough. The mounting portion holes 32 of the spacing bracket 28 are sized, configured and positioned so as to align with the holes 26 of the clevis 24. Once the mounting portion holes 32 are aligned with the clevis holes 26, a pin 34 is disposed through the respective holes 32, 26 thus securing the linear actuator to the mounting bracket 28. In this way, the linear actuator 20 is securely mounted to the base plate 14. It is distinctly understood, however, that any suitable means of mounting the linear actuator 20 to the base plate 14 may be utilized.

The linear actuator 20 has a housing 38, an extendible shaft 40 and an electric motor 36. Disposed substantially within the housing 38 is the extendible shaft 40. The housing 38 and the shaft 40 are preferably disposed longitudinally along the traction device 10. The motor 36 operates to move the shaft 40 relative to the housing 38 bidirectionally and longitudinally. Extendible shaft 40 has a first end 42 which connects to the carriage assembly 22 as will be described in greater detail below.

The linear actuator 20 operates such that when the motor 36 runs in one direction, the first end 42 of the extendible shaft 40 is caused to move outward from the linear actuator housing 38 and to move away from the first end 16 of the base plate 14 and towards the second end 18 of the base plate 14. The linear actuator 20 further operates such that when the motor 36 runs in an opposite direction, the extendible shaft 40 is caused to be retracted into the linear actuator housing 38 with the first end 42 of the extendible shaft 40 being moved towards the first end 16 of the base plate 14 and away from the second end 18 of the base plate 14. Thus, the carriage assembly 22 is moved either towards or away from the first end 16 of the base plate 14, depending upon the direction of the motor 36.

The preferred linear actuator 20 is a Motion Systems Corporation Model 85615 Ball Drive Actuator which utilizes a 24 volts DC, 7400 RPM motor.

A track 44 is provided upon the plate base 14. Although it is preferred that the track 44 be a separate part which is connected to the base plate 14, the track 44 may alternatively be an integral portion of the plate 14. The carriage assembly 22 is then movably connected to the track 44. The carriage assembly 22 is generally constructed of two separate slide portions 48, 50. The first slide portion 48 and the second slide portion 50 may be movably connected to the track 44 by any suitable and convenient means such as by a slot and groove relationship.

The first slide portion 48 preferably has a bracket 52 connected thereto. The first slide portion bracket 52 may be connected to the first slide portion 48 by any convenient means, such as by being integral with the first side portion 48, or, as is preferred, by being a separate component that is attached to the first slide portion 48. The first slide portion bracket 52 may be attached to the first slide portion 48 by any suitable means such as by being bolted thereto.

The first end 42 of the extendible shaft 40 is then connected to the first slide portion bracket 52 of the first slide portion 48. The first end 42 of the extendible shaft 40 may be connected to the first slide portion bracket 52 by any suitable means. Preferably, the first slide portion bracket 52 has a mounting portion 54 having openings 56 provided therethrough. Similarly, the extendible shaft 40 preferably has an opening 58 provided at the shaft first end 42. A pin 60 may then be disposed through the aligned shaft first end opening 58 and the bracket mounting portion opening 56.

A second slide portion 50 is also movably connected to the track 44. The second slide portion 50 is likewise movably connected to the track 44 by any suitable and convenient means such as by a groove and slot relationship. The second slide portion 50 preferably has a bracket 62 mounted thereto. The second slide portion bracket 62 may be connected to the second slide portion 50 by any convenient means, such as by being integral with the second slide portion 50, or, as is preferred, by being a separate component that is attached to the second slide portion 50. The second slide portion bracket 62 may be attached to the second slide portion 50 by any suitable means such as by being welded thereto.

The bracket 52 of the first slide portion 48 preferably has an opening 64 disposed therethrough. Similarly, the bracket 62 of the second slide portion 50 also preferably has an opening 66 disposed therethrough. The first slide portion bracket opening 64 and the second slide portion bracket 66 are preferably configured and positioned so as to be alignable with one another. A bolt 68 is then disposed through the aligned first slide portion bracket opening 64 and the second slide portion bracket opening 66. The bolt 68 is held in position through a nut 70. In this way, the bolt 68 and the nut 70 prevent the first slide portion bracket 52 and the second slide portion bracket 62 from moving away from one another. Thus, the first slide portion 48 and the second slide portion 50 are likewise prevented from moving away from one another.

A spring 72 is provided between the first slide portion bracket 52 and the second slide portion bracket 62. Preferably, the spring 72 is disposed around the bolt 68. In this way, the first slide portion bracket 52 and the second slide portion bracket 62 may move toward one another by overcoming the resistance provided by the spring 72. Although the spring 72 is preferably a helical spring, any type of spring may be used such as a leaf spring or a section of resilient material.

It is further preferred that a member 74 is connected to the second slide portion 50. The member 74 may be connected to the second slide portion 50 by any convenient means, such as by being integral with the second slide portion 50 or by being a separate component that is attached to the second slide portion 50. The member 74 may also be connected to the second slide portion 50 by being attached to the second slide portion bracket 62.

Base plate 14 preferably has a slot 46 disposed therethrough. The member 74 then preferably extends through the slot 46 of the base plate 14. In this way, the member 74 may move longitudinally along the base plate 14 upon longitudinal movement of the carriage assembly 22 caused by the linear actuator 20. The patient holding device 12 is then connected to the member 74.

A sensor 76 is also preferably provided for determining the amount of traction force applied to a patient by the device 10. As is described in greater detail below, the first slide portion 48 and the second slide portion 50 are moved toward one another (compressing the spring 72 that amount) when traction force is applied to a patient by the device 10. The sensor 76 is preferably an electronic device which determines the distance between the first slide portion 48 and the second slide portion 50. By knowing the spring constant of the spring 72 and the relative distance between the first slide portion 48 and the second slide portion 50, the applied traction force to the patient may be determined. The relationship between the spring constant, the relative distance between the first slot portion 48 and the second slot portion 50 and the applied traction force is provided by the equation $F=K\times D$, where F equals the traction force (pounds), K equals spring constant (pounds/inch) and D equals distance spring is compressed (inches). It is understood that to measure the distance between the first slide portion 48 and the second slide portion 50, the sensor may actually measure the distance between the first slide portion 48 itself, the shaft 40, first slide portion bracket 52 or any structural element rigidly connected to the first slide portion 48 and the second slide portion 50 itself, the second slide portion bracket 62, the member 74 or any structural element rigidly connected to the second slide portion 50.

Figure 6:
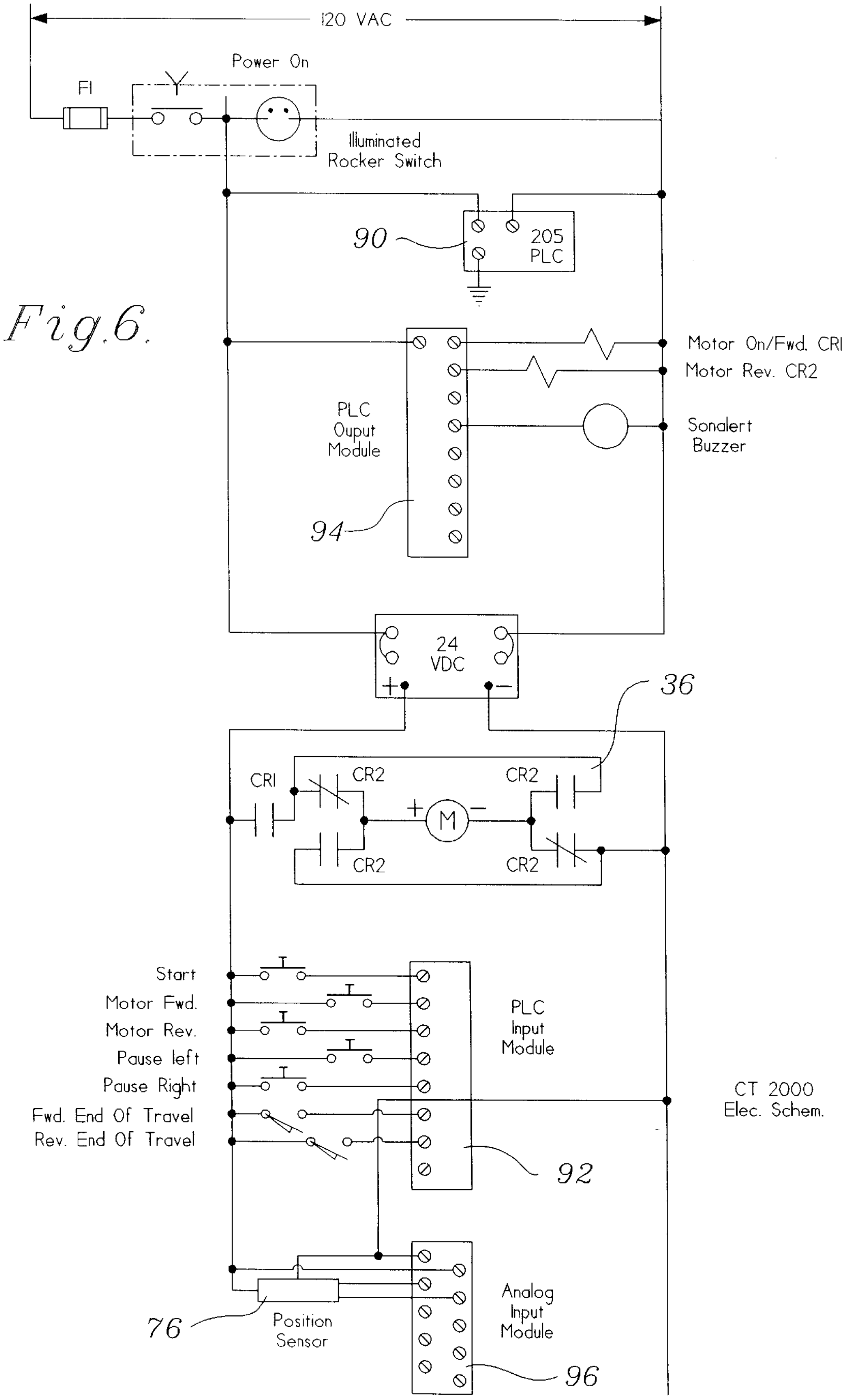
FIG. 6 is a schematic showing the electrical components of the present preferred electro-mechanical traction device.

A programmable logic control device 90 is also preferably utilized. The output from the sensor 76 is provided to the programmable logic control device. The programmable logic control (PLC) device 90 has an input module 92 and an output module 94 which are operatively connected to the motor 36 to activate the linear activator 20 in order to either provide or relax the traction force. A simple block diagram showing the electrical components of the device is shown in FIG. 6.

The preferred programmable logic control device 90 is a Koyo Model DL205 Programmable Logic Controller. It utilizes a DL230 central processing unit with a built-in RS232 communications port. Inputs are handled by a DC input module and outputs are handled by a Relay output module. The tension values, the time values and the repeat values for the device are input into the programmable logic control device 90 through the use of an operator interface unit. These values are stored in memory registers and used for comparison with actual values. Tension control is accomplished by using an analog input module 96 in conjunction with a position sensor 76. The preferred position sensor is a Gordon Products, Inc. Model EA30 Analog Proximity Sensor. The sensor 76 outputs a voltage that is proportional to the distance from the sensor target. As described above, the sensor 76 detects the distance in which the spring is compressed, and therefore, the amount of tension applied to the patient is traction. As the distance changes, the sensor 76 preferably generates a voltage between 1 and 5 volts DC. This voltage is then input into one channel of the analog input module 96. The analog input module converts the voltage reading into a digital value that is then stored in an accumulator in the programmable logic control device 90. The value in the accumulator can be compared to the present value entered by an operator. When the two values are equal, the motor will be stopped. If the value exceeds preselected safety limits, the motor will be reversed and sent to a home position and await for operator action.

Figure 7:
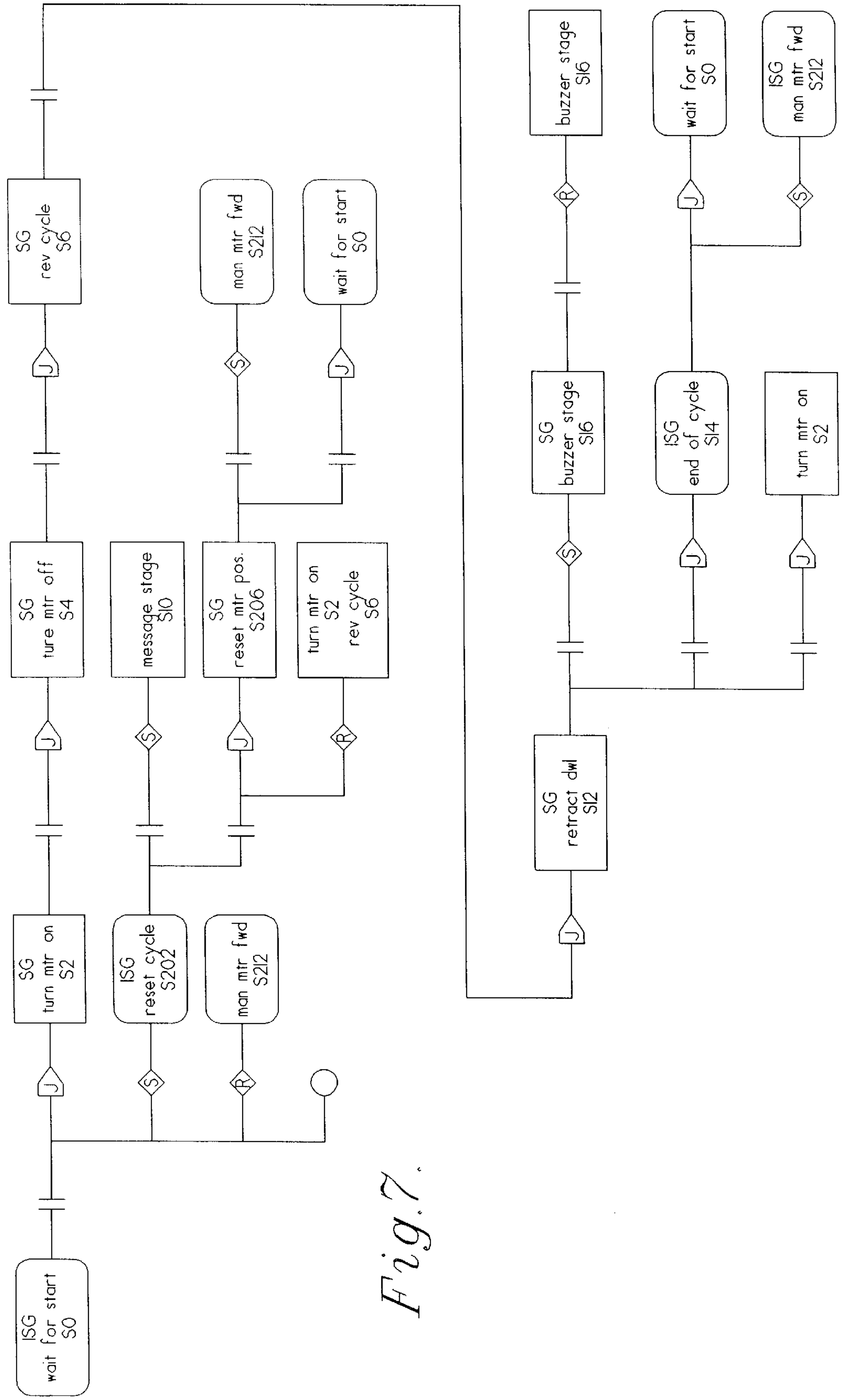
FIG. 7 is a logic flow diagram for the preferred electro-mechanical traction device.

The logic flow for the present invention will now be described with reference to the logic flow diagram of FIG. 7. The logic flow diagram shows the stages to the logic and the relationship to other stages. The following symbols are used in the stage view:

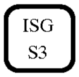

Represents the definition of an initial stage. The definition of a particular initial stage will appear once in the diagram, and all other times it will appear as a reference to the initial stage.

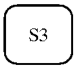

Represents a reference to an initial stage. The definition of the stage will appear elsewhere in the diagram.

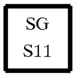

Represents the definition of a stage. The definition of a particular stage will appear once in the diagram, and all other times it will appear as a reference to the stage.

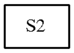

Represents a reference to a stage. The definition of the stage will appear elsewhere in the diagram.

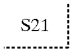

Represents a stage which is referenced by a set, reset, or jump but was not defined in the diagram.

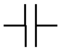

Represents transmission logic

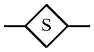

Represents a Set stage coil

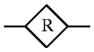

Represents Reset stage coil

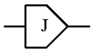

Represents a Jump to stage coil

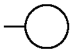

Represents non-stage output logic which appears on a rung with a set, reset, or jump.

The logic flow is as follows:

wait for start (SO)

Stage 0

If the Start switch is pressed, the following occurs:

1. Resets the repeat counter, if the repeat counter has reached its present value.
2. Jump to the "Turn motor on" stage. (Stage 2)
3. Enables "Reset cycle" stage. (Stage 202)
4. Disables the "Manual Motor Forward" Stage. (Stage 212)
5. Resets the Buzzer counter.

turn mtr on (S2)

Stage 2

This stage turns on the motor in the extend direction.

It stays on until the tension value is reached.

When the tension value is reached the program jumps to Stage 4, where the motor is turned off.

turn mtr off (S4)

Stage 4

This stage turns the motor off for the extend time set by the operator. This extend time is located in memory location V2000.

If the tension value is not seen during this stage the motor will be turned on until the tension value is again reached.

When the extend time is over, the motor will reverse to relieve the tension.

rev cycle (S6)

Stage 6

This stage retracts the motor to the home position. If the home value is not found the motor is turned off after a short time delay.

It jumps the program to stage 12 which starts the retract time, looks for the repeat count complete to turn on the end of cycle buzzer (stage 16) and jumps to the end of cycle (stage 14).

If the repeat counter is not complete, the program jumps to Stage 2 to turn the motor on in the extend direction.

retract dwl (S12)

Stage 12

This stage is for the retract time. In this stage the motor is turned off until the delay is over, then the program is jumped to the motor extend stage (Stage 2).

If the repeat counter is enabled then the program is jumped to the end of cycle stage (stage 14) and the buzzer stage is enabled (stage 16).

end of cycle (S14)

Stage 14

This is the end of cycle stage. This stage enables the manual motor buttons again and jumps to Stage 0 to wait for a start signal.

buzzer stage (S16)

Stage 16

This stage controls the duration and number of times the end of cycle buzzer is on and off.

reset cycle (S202)

Stage 202

This stage monitors the pause switches, the overtension value and additional timeout error elements, c3 and c4.

If any of the above conditions are met, the motor fwd and reverse stages are disabled (stage 2 and Stage 6) and the program jumps to Stage 206.

Stage 206 takes control and reverses the motor to relieve the tension.

reset mtr pos. (S206)

Stage 206

This stage is enabled by stage 202, the rest cycle stage.

If any pause button, or the overtension value, or any error timer is detected the motor is instantly reversed to the home position, or reversed for a time delay if the home value is not reached.

The manual switches are enabled and the program is jumped to the Stage 0 to wait for a start signal.

man mtr fwd (S212)
Stage 212
This stage enables the manual motor position switches.
The motor will move in the direction of the pressed switch.
Pressing the forward button disables the reverse button, and pressing the reverse button disables the forward button.

The operation of the traction device 10 in providing a softer traction force will now be discussed with reference to FIGS. 1, 4 and 5. Referring first to FIG. 1, the traction device 10 is shown in a retracted position. In the retracted position, the shaft 40 is substantially disposed within the housing 38 of the linear actuator 20 so that the first end 42 of the extendible shaft 40 is being towards the first end 16 of the base plate 14 and away from the second end 18 of the base plate 14. The shaft 40 of the linear actuator carries the carriage assembly 22 along the track 44 in the direction towards the first end 16 of the base plate 14. Likewise, the patient holding device 12 which is connected to second slide portion 50 of the carriage assembly 22 is moved toward the first end 16 of the base plate 14 as well. The patient and the device 10 are oriented relative to one another such that when the patient holding device 12 is moved in this direction, the traction force applied to the patient is reduced or eliminated.

In the retracted position, a traction force is not being applied to the patient, thus, no external forces arc acting on the device 10. Therefore, the spring 72 acts to move the first slide portion bracket 52 and the second slide portion bracket 62, and thus the first slide portion 48 and the second slide portion 50, away from one another. The first and second slide portion brackets 52, 62 (and thus the first and second slide portion 48, 50) are prevented from being moved apart more than a predetermined spacing distance (designated as "X" in FIG. 1) by the bolt 68 and the nut 70. However, the bolt 68 and nut 70 do not prevent the first and second slide portion brackets 52, 62 from moving towards one another as described below. The preselected spacing distance between the brackets 52, 62 may be adjusted.

Figure 4:
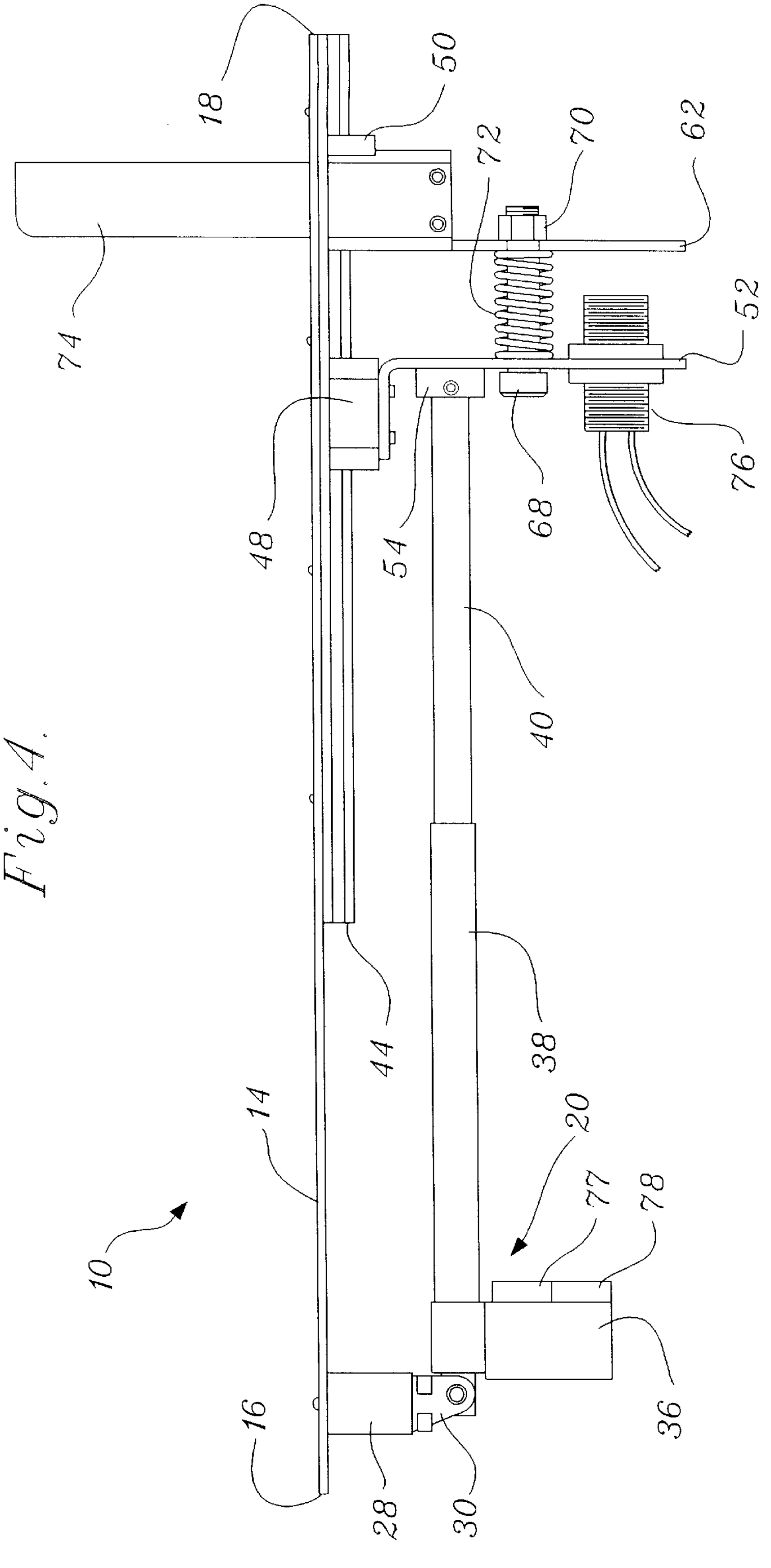
FIG. 4 is a side elevation view of the present preferred electro-mechanical traction device in a partially extended position.

Referring next to FIG. 4, the device 10 is shown in a partially extended position (with no patient holding device shown). The motor 36 is activated so that the first end 42 of the extendible shaft 40 is caused to move outward from the linear actuator housing 38 and to move away from the first end 16 of the base plate 14 and towards the second end 18 of the base plate 14. The shaft 40 in turn causes the first slide portion 48 to move in this direction as well through the connection of the shaft 40 with the first slide portion bracket 52. As the first slide portion 48 is moved, the motion is transmitted through the spring 72 to the second slide portion 50, moving the second slide portion 50 towards the second end 18 of the base plate 14. The patient engaging device 12 connected to the second slide portion 50 is in turn moved, eliminating any slack between the patient engaging device 12 and the patient.

Figure 5:
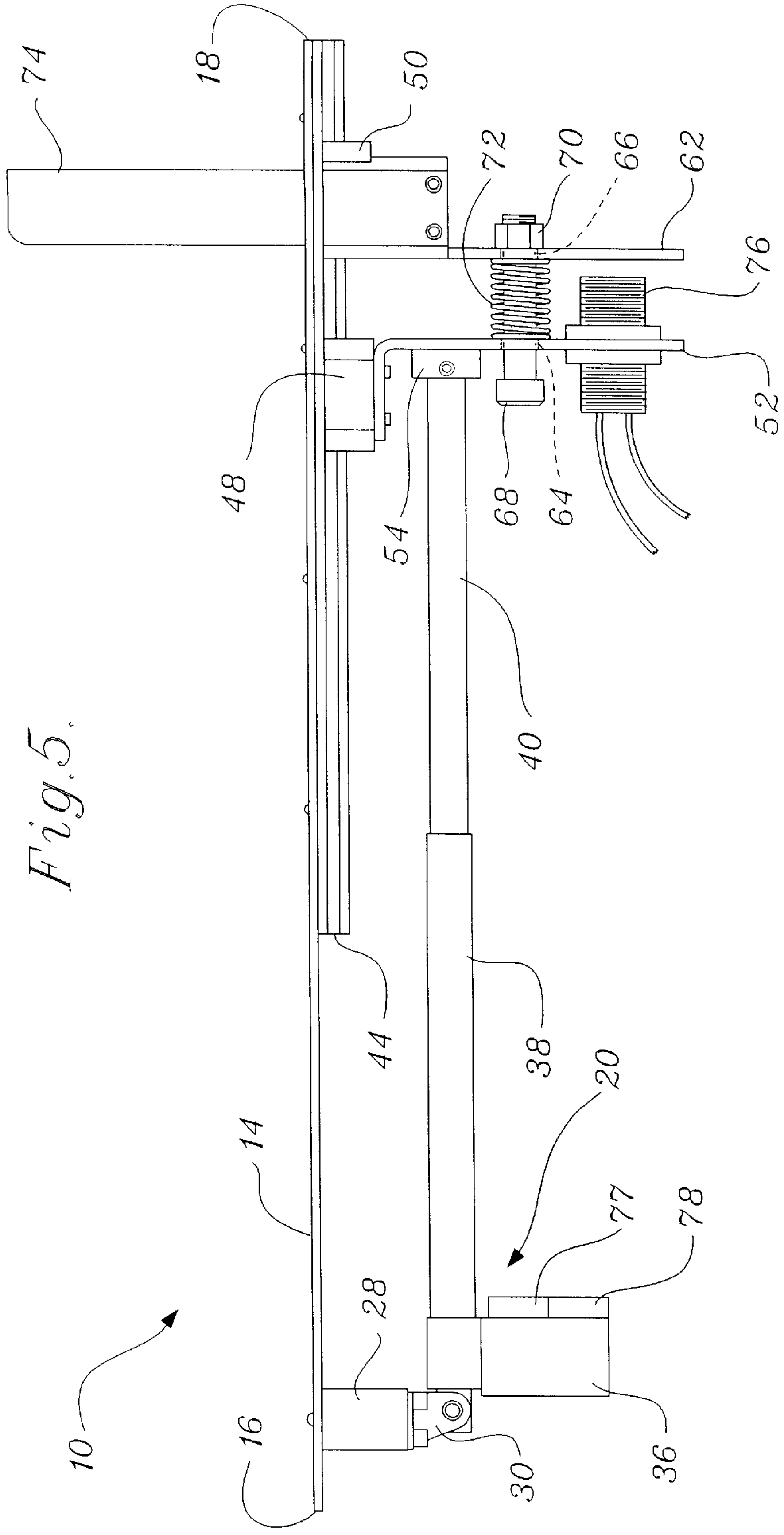
FIG. 5 is a side elevation view of the present preferred electro-mechanical traction device in a more fully extended position.

Referring next to FIG. 5, the device 10 is shown in a more fully extended position in which the traction force is being applied to the patient (and no patient holding device is shown). The motor 36 is activated so that the first end 42 of the extendible shaft 40 is caused to further move outward from the linear actuator housing 38 and to move further away from the first end 16 of the base plate 14 and further towards the second end 18 of the base plate 14. The shaft 40 in turn causes the first slide portion 48 to move further toward the second end 18 of the base plate 14. The movement of the patient holding device 12 and in turn the second slide portion 50 are initially resisted by the patient. Thus, some of the force exerted by the shaft 40 from the motor 36 is stored in spring 72 once that traction force is resisted by the patient. This causes the first and second slide portion brackets 52, 62 and thus the first and second slide portions 48, 50 to compress the spring 72 and to move towards one another. Thus, the traction force developed by the motor 36 is applied softly to the patient. Furthermore, the distance between the first and second slide portions 48, 50 will be related to the amount of traction force applied to the patient by the device 10.

When the direction of the motor 36 is reversed, the shaft 40 is retracted in a direction towards the first end 16 of the base plate 14. The force exerted by the spring 72 on the second slide portion 50 is thus gradually relieved until there is once again slack between the patient and the patient engaging device 12 (shown in FIG. 1). The forces compressing the spring 72 are removed and the spring 72 again forces the first and second slide portions 48, 50 back to their preselected distance X.

The traction device also preferably includes a timer 77 (shown in FIG. 1) for regulating the amount of time in which the linear actuator 20 maintains traction and likewise releases traction. A counter and an audible signal 78 (shown in FIG. 1) are also provided to automatically end the treatment (i.e., the cycle of applying and relaxing the traction force) and to signal the end of the treatment.

With the present invention, a light weight, sturdy traction device is provide which is portable and quiet. It is versatile as it can be used to provide traction to various parts of the human body. It is a "softer" system which provides more tolerance in the traction process which is not otherwise available with direct drive or pneumatic systems now available in the marketplace.

While the fundamental novel features of the invention have been shown and described through certain present preferred embodiments herein, it should be distinctly understood that the invention is not limited thereto but that various substitutions, modifications and variations may be made by those skilled in the art without departing from the spirit or scope of the invention. Accordingly, all such substitutions, modifications or variations are included in the scope of the invention as described by the following claims.

We claim:

1. A portable traction device comprising:

(a) a linear actuator having a movable shaft, wherein the linear actuator may be selectively activated so as to move the shaft in one direction to apply a traction force and to move the shaft in an opposite direction to relax the traction force;

(b) a carriage assembly connected to the shaft and movably connected to a track, wherein the carriage assembly includes (i) a first movable slide portion that is connected to the linear actuator shaft;

(ii) a second movable slide portion spaced a selected distance from the first slide portion;

(iii) a spring disposed between the first and the second slide portions; and (iv) means for connecting the first slide portion to the second slide portion such that the first and the second slide portions are prevented from being moved apart a distance greater than the selected spacing distance but may be moved toward one another by overcoming the spring; and (c) a patient engaging means connected to the second movable slide portion.

2. The portable traction device of claim 1 further comprising a motor operatively connected to the linear actuator for driving the linear actuator.

3. The portable traction device of claim 2 further comprising electrical control means operatively connected to the linear actuator through the motor, wherein when the motor is actuated, the linear actuator applies a traction force to the traction device and when the motor is reversed, the traction force applied to the traction device is relaxed.

4. The portable traction device of claim 1 further comprising a programmable logic control device which causes the linear actuator to exert a predetermined amount of traction force for a predetermined amount of time and to relax the traction force for a predetermined amount of time.

5. The portable traction device of claim 1 further comprising a sensor for determining the amount of traction force applied by the device by determining a relative distance between the first slide portion and the second slide portion.

6. The portable traction device of claim 3 further comprising a sensor for determining the amount of traction force applied by the device by determining a relative distance between the first slide portion and the second slide portion.

7. The portable traction device of claim 6 wherein the electrical control means comprises a programmable logic control device operatively connected to the sensor, wherein the logic device causes the linear actuator to exert a predetermined amount of traction force for a predetermined amount of time and to relax the traction force for a predetermined amount of time.

* * * * *